US006949671B2

(12) United States Patent
Gracey et al.

(10) Patent No.: US 6,949,671 B2
(45) Date of Patent: Sep. 27, 2005

(54) PROCESS FOR THE PRODUCTION OF ACETIC ACID C4-ESTERS

(75) Inventors: Benjamin Patrick Gracey, Hull (GB); Nicholas John Hazel, East Yorkshire (GB)

(73) Assignee: The University of Southern Mississippi Research Foundation, Hattiesburg, MS (US)

( * ) Notice: Subject to any disclaimer, the term of this patent is extended or adjusted under 35 U.S.C. 154(b) by 0 days.

(21) Appl. No.: 10/487,450

(22) PCT Filed: Aug. 28, 2002

(86) PCT No.: PCT/GB02/03930

§ 371 (c)(1),
(2), (4) Date: Jun. 16, 2004

(87) PCT Pub. No.: WO03/020681

PCT Pub. Date: Mar. 13, 2003

(65) Prior Publication Data

US 2004/0249192 A1 Dec. 9, 2004

(30) Foreign Application Priority Data

Aug. 30, 2001 (GB) ........................................... 01209899

(51) Int. Cl.$^7$ ............................................... C07C 67/04
(52) U.S. Cl. ....................................................... 560/247
(58) Field of Search ........................................ 560/247

(56) References Cited

FOREIGN PATENT DOCUMENTS

| DE | 31 05 399 A | 10/1982 |
|----|-------------|---------|
| WO | WO 00/26175 | 5/2000 |

*Primary Examiner*—Paul A. Zucker
(74) *Attorney, Agent, or Firm*—Welsh & Katz, Ltd.

(57) ABSTRACT

Process for treating a mixed $C_4$ stream comprising iso-butene and 1,3-butadiene by (a) reacting the stream with acetic acid in an addition reactor, (b) withdrawing product comprising iso-butene acetate, sec-butenyl acetate, n-butenyl acetate and t-butyl acetate, and recovering n-butenyl acetate from the product and separating and recycling t-butyl acetate to the addition reactor. The process provides increased efficiency of acetic acid utilisation together with useful products, e.g. n-butenyl and sec-butenyl acetates which can be separated and sold as such or converted to other products. The unreacted isobutene can be separated and used as such, or recycled and allowed to dimerise to di-isobutene, another useful product.

16 Claims, No Drawings

PROCESS FOR THE PRODUCTION OF ACETIC ACID C4-ESTERS

This application is the U.S. National Phase of International Application PCT/GB02/03930, filed 28 Aug. 2002, which designated the U.S.

This invention relates to a process for treating a mixed $C_4$ stream comprising iso-butene and 1,3-butadiene.

In naphtha steam-cracking, naphtha is decomposed in the presence of a steam diluent at a temperature between 700 and 900° C. The process produces a number of products, including isomeric butanes, 1,3-butadiene and isomeric butenes (e.g. 1-butene, 2-butene and iso-butene). These compounds may be separated as a mixed $C_4$ stream.

As described in WO 00/26175, mixed $C_4$ streams may be contacted with acetic acid in the presence of a catalyst. Under the reaction conditions, butadiene in the $C_4$ stream reacts with acetic acid to produce n-butenyl and sec-butenyl acetate. The sec-isomer may be recycled to the reactor. The n-isomer, on the other hand, is recovered and hydrogenated to produce n-butyl acetate which is a useful solvent.

Not all the acetic acid initially fed to the reactor is consumed in the butadiene/acetic acid addition reaction. Instead, some of the acetic acid reacts with the iso-butene present in the mixed $C_4$ feedstock to produce t-butyl acetate. This by-product is isolated from the product mixture and cracked back to iso-butene and acetic acid. The iso-butene is recovered by distillation, and sold, for example, as a feedstock for the production of polyisobutene (PIB). The acetic acid is recycled to the reactor, and may be re-consumed in one of the addition reactions occurring therein.

The cracking and distillation equipment required in the process of WO 00/26175 can add cost and complexity to the overall process. It is therefore among the objects of the present invention to provide an alternative process for treating such mixed $C_4$ streams.

According to the present invention, there is provided a process for treating a mixed $C_4$ stream comprising iso-butene and 1,3-butadiene, said process comprising:
 a) reacting acetic acid with said stream in an addition reactor,
 b) withdrawing from the addition reactor a product stream comprising iso-butene, sec-butenyl acetate, n-butenyl acetate and t-butyl acetate, and
 c) recovering n-butenyl acetate from the product stream, characterised in that
 d) t-butyl acetate is recycled to said addition reactor.

For the avoidance of doubt, sec-butenyl acetate and n-butenyl acetate have the following structures:
sec-butenyl acetate

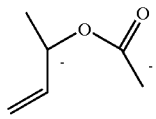

n-butenyl acetate

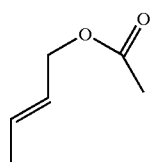

Under the operating conditions of the addition reactor, isobutene and acetic acid react together reversibly to form t-butyl acetate and hence under stable operating conditions isobutene, acetic acid and tertiarybutyl acetate are substantially in equilibrium. Thus, by recycling the t-butyl acetate back to the reactor, the amount of t-butyl acetate in the reaction loop eventually approaches a substantially constant value. By controlling the amount of t-butyl acetate produced in this manner, the amount of acetic acid consumed in the reaction between iso-butene and acetic acid is maintained at a substantially constant level. This leaves a significant proportion of the initial acetic acid feedstock available for desirable reactions, such as the addition reaction with 1,3-butadiene. Although in the present invention iso-butene is preferably not produced by cracking t-butyl acetate as described in WO 00/26175, any unreacted iso-butene present in the original mixed $C_4$ stream may be recovered, for example, by distillation or flash separation techniques.

The mixed $C_4$ stream employed as a feedstock in the present process can be, for example, a by-product of a reaction, such as the dehydrogenation of butane or butene, or the steam cracking of naphtha. Such mixed $C_4$ streams frequently comprise isobutene and 1,3-butadiene. The mixed $C_4$ stream may also comprise one or more of isobutane, n-butane, 1-butene, trans-2-butene, cis-2-butene, 1,2-butadiene, propadiene, methyl acetylene, ethyl acetylene, dimethyl acetylene, vinyl acetylene, diacetylene, and $C_5$ acetylenes. In one embodiment of the present invention, the mixed $C_4$ stream is a by-product of naphtha steam cracking comprising isobutane (e.g. 1–2% v/v), n-butane (e.g. 2–4% v/v), isobutene (e.g. 25–29% v/v), 1-butene (e.g. 8–10% v/v), trans-2-butene (e.g. 6–8% v/v), cis-2-butene (e.g. 3–5% v/v), 1,3-butadiene (e.g. 43–48% v/v), 1,2-butadiene (e.g. 0–2% v/v), propadiene (e.g. 0–1% v/v), methyl acetylene (e.g. 0–1% v/v), ethyl acetylene (e.g. 0–1% v/v), dimethyl acetylene (e.g. 0–1% v/v), vinyl acetylene (e.g. 0–1% v/v), diacetylene (e.g. 0- trace) and $C_5$ acetylenes (e.g. 0- trace). It should be understood that the precise composition of the latter stream may vary depending on factors such as the naphtha feed composition and the how the cracker is operated.

As described in step a), the mixed $C_4$ stream is reacted with acetic acid in an addition reactor. The reaction conditions employed in the addition step are described in detail in WO 00/26175. The relative mole ratios of butadiene in the mixed $C_4$ stream to acetic acid maybe 5:1 to 1:50, preferably, 1:1 to 1:10.

The addition reaction may be carried out at a temperature of 20 to 140° C., preferably, of 40 to 90° C. The reaction may be carried out using a homogeneous or heterogeneous catalyst, the latter being preferred. Suitable catalysts include acidic catalysts such as zeolites, and strong acid ion-exchange resins. Suitable ion-exchange resins include Amberlyst 15® and Amberlite IR120®. A proportion of the acidic sites of such resins may be exchanged with bulky counterions such as alkyl pyridinium, quaternary alkyl ammonium, quaternary arsonium and quaternary phosphonium compounds. Tetra-phenylpbosphonium counterions, for example, may be employed. These counterions may account for up to 10% of the available acidic sites.

Water may be present in the addition step in an amount between 0.05 and 50% w/w, preferably, 0.5 and 20 w/w %, based on the total charge to the reactor.

In certain cases, the activity of heterogeneous catalysts may decrease after prolonged use. This may be due to blockage of active sites by 1,3-butadiene oligo- and polymerisation products. In such cases,-it may be advantageous to carry out the addition reaction under conditions of high shear, as high shear rates are believed to reduce blockage of active sites by the formation of such oligo- and polymerisation products. Alternatively or additionally, polymerisation inhibitors may be added to the reaction mixture. Such inhibitors are well known in the art. Where oligo- and polymerisation products are present in the product stream, however, these may be recovered and recycled to the reactor.

The addition reaction may be carried out using any suitable reactor. For example, a fixed bed, slurry, trickle bed, bus loop, or fluidised bed reactor may be employed.

The reaction between the mixed $C_4$ stream and acetic acid produces a product stream, which is withdrawn from the addition reactor in step b). This product stream comprises addition products including, inter alia, n-butenyl acetate, sec-butenyl acetate and t-butyl acetate. Preferably, such addition products account for 1 to 99% w/w, for example, 5 to 50% w/w of the product stream. The n-butenyl and sec-butenyl acetates result from the addition of acetic acid to butadiene, whilst the t-butyl acetate results from the reaction between acetic acid and iso-butene. Such addition reactions, however, do not generally go to completion and are controlled by a number of factors including how the reaction is conducted (e.g. LHSV), reaction kinetics and equilibrium constants. For this reason, unreacted isobutene and, optionally, unreacted 1,3- butadiene are also present in the product stream. These unreacted $C_4$ components are relatively volatile, and may be separated, for example, by gas disengagement using any suitable separation unit, such as a flash drum. During such a separation step, other volatile $C_4$ components in the product stream, such as unreacted isomeric butanes, 1-butene and 2-butene may also be separated. Where butadiene is present in the separated mixture, the separated mixture may be selectively hydrogenated. This selective hydrogenation step predominantly converts butadiene to 1-butene. Additionally, some isomerisation to 2-butene can occur, as well as further hydrogenation to butane.

The separated mixture of unreacted $C_4$ components may be used as a feedstock, for example, for alkylation, or for steam cracking. Alternatively, the mixture of unreacted $C_4$ components may be separated (e.g. by physical and/or chemical methods) into one or more components for sale or use. Isobutene, for example, may be recovered and polymerised to produce polyisobutene (PIB). 1-Butene and/or 2-butene may be separated, for example, as a mixture and used as a fuel additive.

In addition to the compounds mentioned above, the product stream may also comprise polymerisation by-products such as $C_8$ olefins (e.g. di-isobutene from isobutene) octatrienes (e.g. from butadiene+butadiene) and octadienes (e.g. from butadiene and isobutene), $C_{12}$ olefins ( e.g. from vinyl cyclohexene+butadiene, or $C_8$ olefin+butadiene), $C_8$ acetates, $C_{12}$ acetates and higher oligomeric materials. It may be desirable to remove one or more of such components from the product stream, for example, by distillation. Di-isobutene recovered from the product stream can, if desired, be converted by hydrogenation to iso-octane, a valuable fuel additive.

In step c), n-butenyl acetate is recovered from the product stream. This may be carried out using any suitable separating unit, for example, one or more distillation columns. An example of a suitable apparatus for performing such separation steps is described in WO 00/26175, particularly with reference to Figure 2 of that document. The full disclosure of WO 00/26175 is incorporated herein by reference. Once recovered, the n-butenyl acetate may be, if desired, cracked back to butadiene and acetic acid, or recycled to the reactor. Where the n-butenyl acetate is cracked back to butadiene and acetic acid, at least one of these components may be recycled to the reactor.

Preferably the recovered n-butenyl acetate is hydrogenated to produce butyl acetate. The hydrogenation may be, for example, carried out under heterogeneous conditions over any suitable catalyst. Examples of suitable catalysts include ruthenium, platinum, nickel (e.g. Raneynickel) and palladium. These metals may be employed as elemental metals or metal compounds. Although unsupported catalysts may be employed, it is preferable to use catalysts supported on inert carriers, such as carbon or siliceous supports. Preferred catalysts include supported Raney nickels, and ruthenium on carbon.

The hydrogenation may, for example, be carried out at 20 to 250° C., preferably, 40 to 200° C. The hydrogenation maybe, for example, carried at a pressure of 1 to 100 barg, preferably, 5 to 50 barg. The hydrogenation can be carried out, for example, in slurry and/or flow reactors.

As described in step d), t-butyl acetate is recovered from the product stream and recycled to the reactor. The recovery step may be carried out using any suitable separating unit, for example, a distillation column. The recovered t-butyl acetate stream may also contain other reaction products and/or unreacted reactants including, for example, water and unreacted $C_4$ compounds.

Optionally, sec-butenyl acetate may be recovered from the product stream. The separated sec-butenyl acetate may be recycled to the reactor, or isolated for, for example, sale, direct use (eg as a solvent), or further processing. In one embodiment of the invention, the sec-butenyl acetate is thermally cracked back to butadiene and acetic acid. One or both of these starting materials may be recycled to the reactor, or sold as such.

As described above, t-butyl acetate, n-butenyl acetate and sec-butenyl acetate are recoverable from the product stream. This may be achieved by conventional methods, for example, by distillation. In certain cases, however, the components of the product stream have relatively similar boiling points. This may make conventional distillation difficult.

In a preferred embodiment, components of the product stream comprising t-butyl acetate, n-butenyl acetate and sec-butenyl acetate may be separated from said product stream by azeotropic separative methods, for example using an azeotroping column. This technique involves, for example, introducing the product stream into an azeotroping column in the presence of water. Under these conditions, it is possible to form water/t-butyl acetate/n-butenyl acetate/sec-butenyl azeotrope(s). The azeotrope may be recovered as a process stream, preferably, from an upper portion of the azeotroping column, more preferably, as an overhead stream. When this process stream is allowed to settle, the organic components of the azeotrope, namely, t-butyl acetate, n-butenyl acetate and sec-butenyl may form a layer separate from the water and may be decanted therefrom.

Any residual water may be removed from the decanted mixture by drying the mixture further, for example, using molecular sieve treatment or azeotropic drying. If desired, the azeotroping technique can be adapted by employing an organic azeotroping agent, for example, cyclohexane. Water separated in this manner may be recycled to the azeotroping column. The mixture of t-butyl acetate, n-butenyl acetate and sec-butenyl may then be conveniently separated by conventional distillation techniques. If desired, mixtures of t-butyl acetate and sec-butenyl acetate can be recycled to the reactor thus rendering their separation from one another unnecessary.

A stream comprising unreacted acetic acid and optionally, water and/or reaction by-products maybe recovered from the base of the azeotroping column. This stream may be recycled to the reactor. It may be desirable to purify such streams prior to the recycling step, particularly, when tars are present. This may be achieved by introducing the stream into a settling tank, and allowing the tars to separate from the remainder of the stream as a separate phase. This settling step maybe facilitated by the addition of water.

It should be understood that the azeotropic distillation procedure described above may be applied to any process stream comprising t-butyl acetate, n-butenyl acetate and sec-butenyl acetate.

The invention is illustrated by reference to the following Tests which show how the composition of a C4 stream changes when subjected to treatment with acetic acid in an addition reactor, but without removal and recycle of the products. Hence the Tests illustrate the build-up of by-products, some of which are valuable materials in their own right (e.g. di-isobutene) and some which are regarded of a lesser utility which would be removed at intervals from a commercial process to prevent undue build-up of involatile by-products.

Tests 1 and 2—Reaction of acetic acid with a crude C4 stream

To 2699 g acetic acid and 28 g water was added decane (65 g —to act as an internal standard for subsequent Gas chromatographic analysis), and butylated hydroxytoluene (2.4 g —polymerization inhibitor). The mixture was charged to a 7.5l stainless steel Parr autoclave containing a cooling coil, and supplied with electric band heaters and internal control thermocouple. The catalyst employed was a proprietary sulphonic acid ion exchange resin held captive inside a stainless steel mesh bag fixed around the cooling coil. The action of the agitator enables liquid flow through the catalyst "bed". The vessel was sealed and pressure purged with nitrogen several times (to 10 barg), to remove air. The mixture was then heated with agitation at 1000 rpm to 60 degrees C. (Test 1) and repeated at 70° C. (Test 2). Once at temperature, some 886 g of crude C4 was added to the vessel under nitrogen overpressure. Excess nitrogen was used to increase pressure to desired 40 barg. This gave an acetic acid to butadiene ratio of 4.34:1.

The composition of the crude C4 stream is given in Table 1 below.

Reaction time zero was taken as the moment of C4 addition, and the mixture was maintained at the stated temperature for a period of 4 days while liquid samples were periodically withdrawn and analysed by gas chromatography. The results showed a kinetic profile of product mixture; tertiary-butyl acetate, secondary butenyl acetate and crotyl acetate main products, with lesser amounts of tertiary butanol, C8 olefins and acetates, C12 olefins, 4-vinylcyclohexane and oligomer-by-products, together with unreacted butadiene and acetic acid.

Table 2, below, shows the product composition (analysis by gas chromatography) from Test 1.

For Test 2 (carried out at 70° C.) using the same composition, results are given in Table 3, below.

It can be seen from these static Tests that tertiary butyl acetate forms rapidly under the reaction conditions. It is thus apparent that under suitable working conditions for treating C4 streams in accordance with the present invention, the tertiary butyl acetate can be recycled to an addition reaction, optionally together with other products which may not be desired reaction products. It is also apparent that under the static conditions of Tests 1 and 2 that, after reaching a peak, the concentration of tertiary butyl acetate gradually diminishes. It is believed that this is due to the formation of dimeric or other products either from the tertiary butyl acetate itself or from the isobutene with which it is in equilibrium. It can also be seen from the Tests that, in addition to such useful products as, for example, secondary butenyl acetate and crotyl acetate (which are easily separable from the starting materials), there is a gradual build-up of some other products, e.g., C8 butadiene dimers, C8 acetates and C12 butadiene trimers which are also useful isolable products.

TABLE 1

Composition of Crude C4 stream obtained from Naptha cracker

| Component | Percent (weight) |
| --- | --- |
| Butadiene | 63.2 |
| Butene-1 | 11.1 |
| Butene-2 | 6.9 |
| C3's | 0.1 |
| C5's | 0.015 |
| Isobutane | 1.9 |
| Isobutene | 5.7 |
| N-Butane | 8.9 |
| Total accounted for | 97.815 |

TABLE 2

Product composition profile obtained at 60° C.

| Time (mins) | C8 BD dimers | C8 acetates | C12 BD trimers | Oligomers | t-BuOAc | Sec-BuOAc | Crotyl acetate | 4VCH | t-BuOH |
| --- | --- | --- | --- | --- | --- | --- | --- | --- | --- |
| 0 | 0.32 | 0.03 | 0.03 | 0.01 | 3.99 | 1.34 | 2.07 | 0.00 | 9.41 |
| 29 | 0.55 | 0.05 | 0.07 | 0.01 | 113.14 | 5.25 | 3.35 | 0.06 | 44.04 |
| 64 | 1.25 | 0.27 | 0.23 | 0.02 | 209.38 | 15.84 | 9.19 | 0.06 | 74.01 |
| 93 | 2.16 | 0.43 | 0.45 | 0.03 | 208.85 | 25.33 | 15.14 | 0.08 | 74.54 |
| 142 | 2.92 | 0.74 | 0.71 | 0.04 | 203.24 | 37.26 | 23.07 | 0.11 | 72.73 |
| 202 | 3.12 | 1.20 | 1.14 | 0.10 | 193.07 | 50.94 | 32.51 | 0.17 | 69.93 |
| 269 | 3.70 | 1.65 | 1.55 | 0.23 | 180.62 | 64.80 | 43.12 | 0.20 | 67.37 |
| 322 | 4.17 | 2.11 | 1.99 | 0.45 | 169.08 | 75.83 | 52.79 | 0.25 | 64.74 |
| 425 | 4.65 | 2.69 | 2.53 | 0.78 | 157.52 | 89.71 | 64.66 | 0.31 | 62.17 |
| 1369 | 7.31 | 5.21 | 5.67 | 3.98 | 102.14 | 155.93 | 140.23 | 0.84 | 48.82 |
| 1515 | 7.50 | 8.34 | 6.39 | 4.80 | 91.69 | 167.49 | 154.81 | 0.92 | 45.92 |
| 1645 | 8.07 | 8.86 | 6.68 | 5.23 | 87.95 | 171.96 | 161.12 | 1.01 | 44.74 |
| 1740 | 8.28 | 6.56 | 6.82 | 5.40 | 85.32 | 174.08 | 164.92 | 1.03 | 43.96 |
| 2803 | 9.79 | 8.16 | 7.83 | 7.23 | 68.96 | 185.73 | 183.16 | 1.34 | 38.40 |

TABLE 2-continued

Product composition profile obtained at 60° C.

| Time (mins) | C8 BD dimers | C8 acetates | C12 BD trimers | Oligomers | t-BuOAc | Sec-BuOAc | Crotyl acetate | 4VCH | t-BuOH |
|---|---|---|---|---|---|---|---|---|---|
| 2966 | 10.19 | 11.81 | 8.14 | 7.66 | 64.96 | 186.57 | 187.96 | 1.40 | 37.03 |
| 3326 | 10.61 | 9.03 | 8.37 | 8.23 | 60.94 | 186.65 | 189.67 | 1.45 | 35.53 |
| 4292 | 11.48 | 9.74 | 8.74 | 9.44 | 53.40 | 185.73 | 188.66 | 1.59 | 32.45 |
| 4464 | 11.79 | 10.07 | 8.94 | 9.82 | 50.97 | 183.80 | 188.66 | 1.62 | 31.56 |
| 4614 | 11.91 | 13.64 | 8.98 | 9.44 | 50.08 | 184.25 | 186.96 | 1.62 | 31.17 |
| 4759 | 12.08 | 13.63 | 8.94 | 9.26 | 49.27 | 184.86 | 186.59 | 1.65 | 30.89 |
| 5692 | 12.59 | 14.33 | 9.28 | 10.11 | 43.77 | 176.20 | 182.88 | 1.65 | 28.43 |
| 5816 | 12.86 | 14.55 | 9.40 | 10.50 | 42.56 | 176.04 | 180.45 | 1.68 | 27.90 |
| 5928 | 12.91 | 14.56 | 9.36 | 11.24 | 41.95 | 175.12 | 169.92 | 1.68 | 27.65 |

TABLE 3

Product composition profile obtained at 70° C.

| Time (mins) | C8 BD dimers | C8 acetates | C12 BD trimers | Oligomers | t-BuOAC | sec BuOAc | Crotyl acetate | 4VCH | t-BuOH |
|---|---|---|---|---|---|---|---|---|---|
| 0 | 0.12 | 0.05 | 0.06 | 0.01 | 1.83 | 1.29 | 1.52 | 0.00 | 2.64 |
| 12 | 0.39 | 0.10 | 0.05 | 0.10 | 122.36 | 4.36 | 3.04 | 0.08 | 45.02 |
| 25 | 0.91 | 0.06 | 0.14 | 0.10 | 195.98 | 11.70 | 6.78 | 0.14 | 58.69 |
| 36 | 1.24 | 0.08 | 0.28 | 0.10 | 203.69 | 18.22 | 10.57 | 0.14 | 58.47 |
| 60 | 1.84 | 0.45 | 0.61 | 0.12 | 195.05 | 30.60 | 18.56 | 0.17 | 55.96 |
| 117 | 3.10 | 1.15 | 1.36 | 0.23 | 173.51 | 55.88 | 36.28 | 0.22 | 52.14 |
| 149 | 3.66 | 1.61 | 1.77 | 0.38 | 161.98 | 68.70 | 46.49 | 0.25 | 49.75 |
| 176 | 4.56 | 2.49 | 2.79 | 1.06 | 141.45 | 92.44 | 67.01 | 0.31 | 46.06 |
| 307 | 5.45 | 3.61 | 3.99 | 1.85 | 120.45 | 117.69 | 92.52 | 0.37 | 41.76 |
| 1312 | 8.93 | 6.94 | 7.57 | 5.75 | 70.92 | 170.84 | 158.47 | 0.62 | 29.67 |
| 1434 | 16.20 | 7.80 | 8.38 | 6.58 | 61.98 | 177.00 | 169.52 | 0.65 | 27.11 |
| 1711 | 10.96 | 8.20 | 8.85 | 7.60 | 56.36 | 177.79 | 172.44 | 0.67 | 25.42 |
| 1775 | 10.60 | 8.44 | 8.76 | 7.48 | 54.84 | 179.11 | 173.48 | 0.70 | 24.89 |
| 2770 | 11.60 | 9.42 | 9.68 | 9.17 | 43.79 | 173.63 | 170.31 | 0.73 | 21.18 |
| 2892 | 11.92 | 9.77 | 9.66 | 9.55 | 41.06 | 172.13 | 168.51 | 0.76 | 20.16 |
| 3095 | 13.00 | 9.94 | 10.55 | 9.89 | 39.34 | 170.17 | 169.60 | 0.73 | 19.63 |
| 3209 | 12.91 | 10.04 | 10.18 | 9.91 | 38.33 | 169.21 | 168.99 | 0.76 | 19.21 |
| 4163 | 13.77 | 10.49 | 10.78 | 10.77 | 33.07 | 162.04 | 160.75 | 0.76 | 17.30 |
| 4196 | 13.91 | 10.67 | 10.63 | 11.37 | 31.86 | 159.76 | 158.58 | 0.76 | 16.76 |
| 4224 | 13.86 | 9.08 | 10.89 | 11.01 | 31.89 | 159.99 | 159.14 | 0.76 | 16.82 |

What is claimed is:

1. A process for treating a mixed C4 stream comprising iso-butene and 1,3-butadiene, said process comprising:
   a) reacting acetic acid with said stream in an addition reactor,
   b) withdrawing from the addition reactor a product stream comprising iso-butene, sec-butenyl acetate, n-butenyl acetate and t-butyl acetate, and
   c) recovering n-butenyl acetate from the product stream, characterised in that
   d) t-butyl acetate is recycled to said addition reactor.

2. A process as claimed in claim 1 wherein isobutene is recovered from the product stream.

3. A process as claimed in claim 2 wherein the isobutene is recovered by distillation.

4. A process as claimed in claim 1 wherein isobutene is recycled to the addition reactor.

5. A process as claimed in claim 1 wherein the mixed $C_4$ stream is obtained by the dehydrogenation of butane or butene, or by the steam cracking of naphtha.

6. A process as claimed in claim 1 wherein, in addition to the iso-butene and 1,3-butadiene, the mixed $C_4$ stream comprises one or more of isobutane, n-butane, 1-butene, trans-2-butene, cis-2-butene, 1,2-butadiene, propadiene, methyl acetylene, ethyl acetylene, dimethyl acetylene, vinyl acetylene, diacetylene, and $C_5$ acetylenes.

7. A process as claimed in claim 1 wherein, in the addition reactor, the relative mole ratios of butadiene in the mixed $C_4$ stream to acetic acid is in the range 1:1 to 1:10.

8. A process as claimed in claim 1 wherein the addition reaction is carried out at a temperature in the range 40 to 90° C.

9. A process as claimed in claim 1 wherein the addition reaction is carried out using a heterogeneous catalyst.

10. A process as claimed in claim 9 wherein the heterogeneous catalyst comprises a zeolite or a strong acid ion-exchange resin.

11. A process as claimed in claim 1 wherein water is present in the addition reaction in an amount between 0.5 and 20 w/w %, based on the total charge to the reactor.

12. A process as claimed in claim 9 wherein the addition reaction is carried out under conditions of high shear.

13. A process as claimed in claim 1 wherein a polymerisation inhibitor is added to the addition reaction mixture.

14. A process as claimed in claim 1 wherein the n-butenyl acetate recovered from the product stream is hydrogenated to produce butyl acetate.

15. A process as claimed in claim 1 wherein components of the product stream comprising t-butyl acetate, n-butenyl acetate and sec-butenyl acetate are separated from said product stream by azeotropic separative methods.

16. A process as claimed in claim 1 wherein di-isobutene is recovered from the product stream.

* * * * *